(12) United States Patent
Atala

(10) Patent No.: US 6,620,203 B2
(45) Date of Patent: Sep. 16, 2003

(54) TISSUE ENGINEERED TESTICULAR PROSTHESIS AND USE THEREOF

(76) Inventor: Anthony Atala, 74 Westerly Rd., Weston, MA (US) 02193

(*) Notice: Subject to any disclaimer, the term of this patent is extended or adjusted under 35 U.S.C. 154(b) by 37 days.

(21) Appl. No.: 10/017,921

(22) Filed: Dec. 13, 2001

(65) Prior Publication Data

US 2002/0091448 A1 Jul. 11, 2002

Related U.S. Application Data

(63) Continuation of application No. PCT/US01/13890, filed on Apr. 30, 2001.
(60) Provisional application No. 60/200,427, filed on Apr. 28, 2000.

(51) Int. Cl.⁷ ................................................. A61F 2/36
(52) U.S. Cl. ................................. 623/23.71; 623/23.67
(58) Field of Search ........................... 623/23.75, 6.64, 623/23.64–23.72

(56) References Cited

U.S. PATENT DOCUMENTS

| 5,141,581 A | * | 8/1992 | Markham ................... 156/242 |
| 5,496,370 A | * | 3/1996 | Hamas ..................... 623/23.67 |
| 5,632,777 A | * | 5/1997 | Petrick ........................ 128/898 |
| 5,653,757 A | * | 8/1997 | Petrick ........................ 128/898 |
| 6,093,522 A | | 7/2000 | Kitteridge |
| 6,187,047 B1 | | 2/2001 | Kwan et al. |
| 6,264,702 B1 | | 7/2001 | Ory et al. |

\* cited by examiner

*Primary Examiner*—David H. Willse
*Assistant Examiner*—Hieu Phan
(74) *Attorney, Agent, or Firm*—Nixon Peabody LLP

(57) ABSTRACT

The present invention provides a tissue engineered testicular prosthesis for implanting within a patient having a scaffold with a biodegradable polymer scaffold having a substantially elliptical body in longitudinal cross-section replicating the shape of a testicle and a substantially circular cross-section in transverse cross-section, the biodegradable scaffold defining an interior and an exterior of the prosthesis, and the scaffold being seeded with disassociated chondrocytes or Leydig cells, or both chondrocytes and Leydig cells. The interior of the prosthesis can be at least partially filled with testosterone.

16 Claims, 6 Drawing Sheets

TISSUE ENGINEERED TESTICULAR PROSTHESIS AND USE THEREOF

CROSS-REFERENCE TO RELATED APPLICATIONS

This application is a continuation of copending International Application PCT/US01/13890 filed on Apr. 30, 2001 which designated the U.S and which claims the benefit of U.S. Provisional Application No. 60/200,427, filed Apr. 28, 2000, the content of which is relied upon and incorporated herein by reference in its entirety.

FIELD OF THE INVENTION

The present invention is generally directed to a tissue engineered (TE) testicular prosthesis having both cosmetic and therapeutic uses.

BACKGROUND OF THE INVENTION

Testicular dysfunction, characterized by either an absence of androgenic production, an absence of the testes, or both, has great medical and psychological consequences on the afflicted male population ranging from infertility and cancer to psychiatric disturbances. Causes of testicular dysfunction include chromosomal abnormalities, testicular torsion (which may be a result of inadequate connective tissue within the scrotum or trauma to the scrotum, after strenuous exercise or without an obvious cause; the incidence is higher during infancy and with the onset of adolescence) direct trauma to the testicles, diseases that affect the testicle (such as mumps orchitis and testicular cancer), and a variety of drugs. Increased risk is associated with activities that may cause constant, low level trauma to the scrotum (such as riding a motorcycle) or frequent administration of a drug known to affect testicular function (such as heavy marijuana use or taking some prescription medications). Thus, testicular dysfunction can result at the time of fetal development, adolescence and during the adult years.

During fetal development, the fetal testes are formed within the abdominal cavity in the region where the kidneys are normally located in adults. They descend into their normal scrotal position shortly before birth. The prevalence of undescended testes (cryptorchidism) is 3.4% in full-term infants and as high as 30% in premature infants. The testes often descend after birth, and the prevalence of cryptorchidism by one year of age is down to 1%. Current practice is to surgically correct undescended testes at around age one year. The main reason for bringing the testes down early is to preserve future fertility. Testicular atrophy may be present due to a primary abnormality of the testis or due to damage incurred during surgery. A testicular prosthesis could be inserted for cosmetic reasons, but the undescended testicle may have to be removed to achieve the desired "normal" result. This undescended testes may be producing hormones and be worth sparing. However, the risks of inserting a testicular prosthesis are minimal and consist of infection (around 2%) and bruising. Physicians frequently recommend that a testicular prosthesis be placed early in life to prevent shrinkage of the scrotum which can occur when the sac is empty, and allow for normal psychological development through the patient's early years.

In addition, there is an association between cryptorchidism and testicular cancer. Approximately 10% of testicular tumors arise from an undescended testis, and the risk of malignancy in an undescended testis is thought to be 35-fold higher than for a normal descended testis. The best way to detect testicular cancer is by palpation. Thus, another reason for surgically correcting cryptorchidism is to allow the patient to easily perform monthly self-examination. Yet despite this increased risk, the annual risk of malignancy is estimated to be only one in 2,550 cases. Moreover, the risk of death from removal of the testis is higher than the risk of testicular cancer in patients over 32 years of age.

To date, testicular prosthesis have been of solid material or have been filled with a soft silicone elastomer or a silicone gel. See "The Why and How of Synthetic Replacement Testicles" by Joseph Ortenberg. M.D. and Robert G. Kupper, M.D. in Contemporary Urology. October 1991. pp 23–32. Moreover, no testicular implants have been sold in the U.S. since 1995, when the FDA called for a pre-market approval application on these devices in fear of harmful effect of silicone. As a result, Silicone Gel implants are not available in the U.S., and the American Urological Association have advised against using these products. A Silicone Elastomer prosthesis may be available, and is endorsed for use by the American Urological Association. Hence, alternatives to testicular implants are very limited, leaving patients with few treatment options.

Recently, Mentor Corporation of Santa Barbara, Calif. developed a saline-filled implant which is currently awaiting the FDA approval. The Mentor testicular prosthesis approximates the weight, shape, and feel of a normal testicle. The prosthesis is available in four sizes, extra small, small, medium, and large. The implant consists of a molded silicone-elastomer shell approximately 0.035 inches thick, with a self-sealing injection site located on one end of the prosthesis. The injection site allows the surgeon to fill the implant with sterile, pyrogen-free Sodium Chloride USP solution. On the end opposite of the fill site is a silicone elastomer tab for suturing the prosthesis in place. See U.S. Pat. Nos. 6,060,639 and 5,653,757.

The prosthetic testicles that are available today have a realistic appearance but may feel foreign (hard) and cause discomfort. It is not uncommon for patients to remove the prosthesis several years later due to pain and discomfort. Because artificial testicles do not move as natural testicle do, they sometimes become fixed in peculiar positions thereby causing the scrotum to hang abnormally. Moreover, with the normal developmental growth, corresponding larger testicle sizes must be surgically replaced. With the available prosthetic options, it is often recommended to young patients to attenuate prosthetic placement as long as possible in order to reduce the number of procedures required to maintain the appropriate testicle size. This of course does not address the emotional issues associated with the artificial testicle and numerous replacement surgeries. Additionally, male patients with an absence of testes (anorchia) commonly require testicular prosthesis placement and hormone replacement treatment. Unfortunately, the currently available testicular prosthesis have no capabilities to produce and supply androgenic substances, and the several types of testosterone compounds and various modes of hormone deliver, that are currently used clinically, however, have pharmacokinetic properties that are not ideal.

The testes of male mammals, including humans, is the source of circulating androgens that are responsible for the maintenance of the secondary sexual characteristics in the male. In most species, the testes is divided into two separate compartments: the seminiferous tubules that contain the Sertoli cells, the peritubular cells and the germ cells; and the interstitial compartment that contains the Leydig cells, macrophages, lymphocytes, granulocytes and the cells composing the blood, nerve and lymphatic structures. Leydig cells are interspersed between the various coils of the seminiferous tubules, and are responsible for the production of androgens or male sex hormones.

The Leydig cells, located in the interstitial compartment and comprising approximately 2–3% of the total testicular cell number in most species, are the only testicular cells capable of the first two steps in steroidogenesis; i) the conversion of cholesterol, the substrate for all steroid hormones, to pregnenolone: and ii) conversion of pregnenolone to progesterone. Therefore, the interstitial compartment in general, and the Leydig cells in particular synthesize virtually all of the steroids produced in the testis with testosterone being the major steroid biosynthesized.

The major stimulus for the biosynthesis of testosterone in the Leydig cell is the gonadotrophic hormone, luteinizing hormone (LH). LH is secreted from specific cells located in the anterior pituitary and it interacts with specific receptors on the surface of the Leydig cell and initiates the signal for testosterone production. Cellular events occur rapidly in response to the trophic hormone stimulation of Leydig cells, and result in the synthesis and secretion of testosterone.

Patients with testicular dysfunction require androgen replacement for somatic development. "Androgen" refers to a family of male sex hormones which include, without limitation, testosterone, dihydrotestosterone, and rostenedione. Androgens such as testosterone, play a key role in the development of male sexual characteristics such as growth of the penis, muscles and beard as well as deepening of the voice.

Testosterone therapy is currently indicated for treatment of male hypogonadism, anemia, breast cancer, and hereditary angioedema. It is also being considered for treating a variety of other conditions such as male osteoporosis that appear to be mediated by androgen deficiency.

Traditional modalities for administering testosterone have include: intramuscular injection of long-acting testosterone esters such as the enanthate because testosterone itself is rapidly degraded by the liver if administered orally; oral administration of testosterone undecanoate, which provides systemically available testosterone; and subcutaneous implantation of fused testosterone pellets. However, none of these traditional modalities provides totally physiological levels or circadian patterns of testosterone and its active metabolites, dihydrotestosterone (DHT) and estradiol (E2), and long term non-pulsatile testosterone therapy may cause multiple problems, including erythropoiesis and bone density changes.

For the foregoing reasons and deficiencies of the current state of the art, there exists a need for (1) a TE testicular prosthesis that would not require periodic removal to correct for size changes, and (2) a TE testicular prosthesis that can be used therapeutically in controlled androgen replacement therapy (e.g., testosterone replacement) and long term physiological release of androgens, such as testosterone, without the side-effects encountered in the currently available treatments.

SUMMARY OF THE INVENTION

It is an object of the present invention to provide a tissue-engineered, testicular prosthesis for the purpose of replacing an absent or abnormal testicle in a male patient. It is a further object of this invention to provide a tissue-engineered testicular prosthesis that is therapeutically functional in that it would be able to satisfy the function of a normal testicle by releasing testosterone.

The prosthesis of the present invention is suited for use in male patients of all ages for whom testicular replacement is indicated either with or without the therapeutic release of testosterone, e.g., children with undescended testicles or torsion of the testicle, and adults with testicular cancer, traumatic injury or orchiectomy. The prosthesis of the present invention is especially suited for use in infants or young children.

It is yet another object of the present invention to provide a TE testicular prosthesis capable of providing a controlled androgen replacement therapy and long term physiological release of androgen, such as testosterone, in males in need thereof.

In one aspect of the invention, the TE testicular prosthesis for implanting within a patient comprises a scaffold comprising a biodegradable polymer scaffold having a substantially elliptical body in longitudinal cross-section replicating the shape of a testicle and a substantially circular cross-section in transverse cross-section, the biodegradable scaffold defining an interior and an exterior of the prosthesis, and the scaffold being seeded with disassociated chondrocytes or Leydig cells, or both chondrocytes and Leydig cells. In one embodiment of the invention, the biodegradable polymer scaffold has an inner interconnected mesh network.

The use chondrocytes as a scaffold seed provides the benefit of the resulting testicle to approximate the density of the normal testicle thereby providing a more natural and comfortable feeling to the patient compare to the foreign sensation and sometimes pain that is typically caused a silicone prosthesis.

In another embodiment of the invention, the interior of the TE testicular prosthesis is filled, at least partially, with testosterone for the physiological release of the substance. The physiological release of testosterone typically continues for a time period after which the interior is refilled.

When the scaffold is seeded with Leydig cells alone or with Leydig, cells in combination with chondrocytes, the resulting prosthesis functions both cosmetically and therapeutically as a testosterone production and secretion source.

The seeded scaffold can be cultured in vitro or in vivo. Preferably the seeded scaffold is cultured in vitro prior to implantation in a host. Preferably, the culturing is for a time period sufficient for cartilaginous tissue to form.

The chondrocytes can be autologous, allogenic or xenogenic. Autologous chondrocytes are preferred. In patients lacking testicles, donor Leydig cells can be used.

The term "biodegradable", as used herein refers to materials which are enzymatically or chemically degraded in vivo into simpler chemical species. Either natural or synthetic polymers can be used to form the matrix, although synthetic biodegradable polymers are preferred for reproducibility and controlled release kinetics. Synthetic polymers that can be used include polymers such as poly(lactide) (PLA), poly(glycolic acid) (PGA), poly(lactide-co-glycolide) (PLGA). poly(caprolactone), polycarbonates, polyamides, polyanhydrides, polyamino acids, polyortho esters, polyacetals, polycyanoacrylates and degradable polyurethanes, and non-erodible polymers such as polyacrylates, ethylene-vinyl acetate polymers and other acyl substituted cellulose acetates and derivatives thereof. PGA and PLGA polymers are preferred.

Preferred biodegradable polymers comprise a polymer selected from the group consisting of polyesters of hydroxycarboxylic acids, polyanhydrides of dicarboxylic acids, and copolymers of hydroxy carboxylic acids and dicarboxylic acids. In other embodiments the material is a synthetic polymer derived from at least one of the following monomers: glycolide, lactide, p-dioxanone, caprolactone, trimethylene carbonate, butyrolactone. In preferred embodiments, the material is selected from the group consisting of polymers or copolymers of glycolic acid, lactic acid, and sebacic acid. Polyglycolic acid polymers are most preferred. A polyhydroxyalkanoate (PHA) polymer may also be used. Preferably, the polymer biodegrades in less than 3 months, more preferably, less than 2 months.

It is a further object of the present invention to provides for therapeutic delivery of an androgenic substance, such as testosterone, using a TE testicular prosthesis comprising microencapsulated Leydig cells within the prosthesis. Microencapsulated Leydig cells enable controlled testosterone replacement therapy in addition to offering several advantages, such as serving as a semipermeable barrier between the transplanted cells and the patient's immune system, as well as allowing for the long term physiological release of testosterone. Furthermore, microencapsulated Leydig cells are viable and are able to produce testosterone in vitro and in vivo. The microencapsulation system renders the cells non-immunogenic by employing polymers that serve as an immuno-protective layer surrounding the cell. This technology can be used to replace or supplement testosterone in patients with testicular dysfunction.

In another embodiment the Leydig cells are immortalized with telomerase or by other means before incorporation into the TE testicular prosthesis. Telomerase-immortalized human cells provide more stable, uniform cell populations for long-term gene expression.

Other aspects of the invention are disclosed infra.

BRIEF DESCRIPTION OF THE FIGURES

For a more complete understanding of the invention, reference should be made to the figures, in which:

FIG. 8A is the graph of the entire study period, and FIG. 8B is the enlarged graph of weeks 17–39.

FIG. 9A is the graph of the entire study period, and FIG. 9B is the enlarged graph of weeks 5–14.

DETAILED DESCRIPTION OF THE INVENTION

The present invention provides a tissue-engineered (TE) testicular prosthesis for cosmetic and/or therapeutic use.

Patients with anorchia, cryptorchidism, testicular cancer, ambiguous genitalia and trauma may benefit from testicular prostheses implantation. Several reports have stressed the importance of having both testicles in the scrotum for normal psychosexual development.[4,5] Silicone gel prostheses implantation has been routinely practiced for many years until the moratorium imposed by the American Urological Association in 1992.[6] Although saline-filled Silicone prosthesis are currently under investigation, the biocompatibility issues are still unresolved.

In accordance with the present invention, we have discovered that cartilaginous testicular prostheses can be engineered in vitro and in vivo using chondrocytes seeded on pre-configured testis-shaped polymer scaffolds. We found that cartilage testicular prostheses can be designed to accommodate high concentrations of testosterone, which allows for its slow release, maintaining physiologic levels over time.

Figure 4:
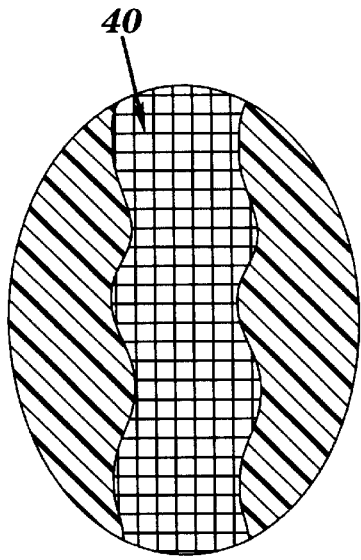
FIG. 4 illustrates an inner interconnected mesh network (40) of the testicular prosthesis.
Figure 2:
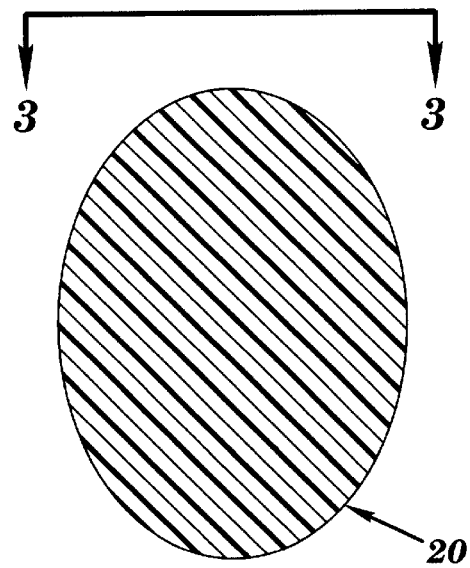
FIG. 2 illustrates a cross-sectional view along line 2—2 of FIG. 1 of a substantially elliptical body (20) of the testicular prosthesis.
Figure 3:
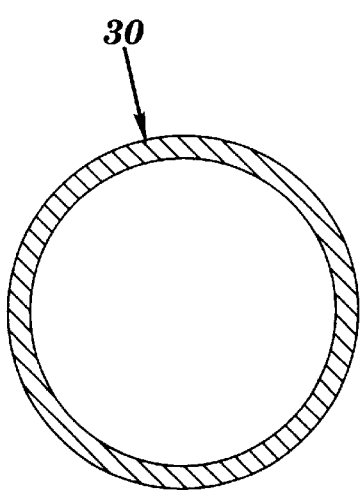
FIG. 3 illustrates a cross-sectional view along line 3—3 of FIG. 2 of a substantially circular cross section (30) of the testicular prosthesis.
Figure 1:
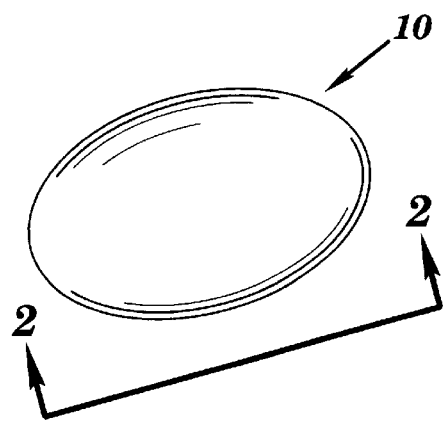
FIG. 1 illustrates a perspective view of a testicular prosthesis (10) of the present invention.
Figure 5B:
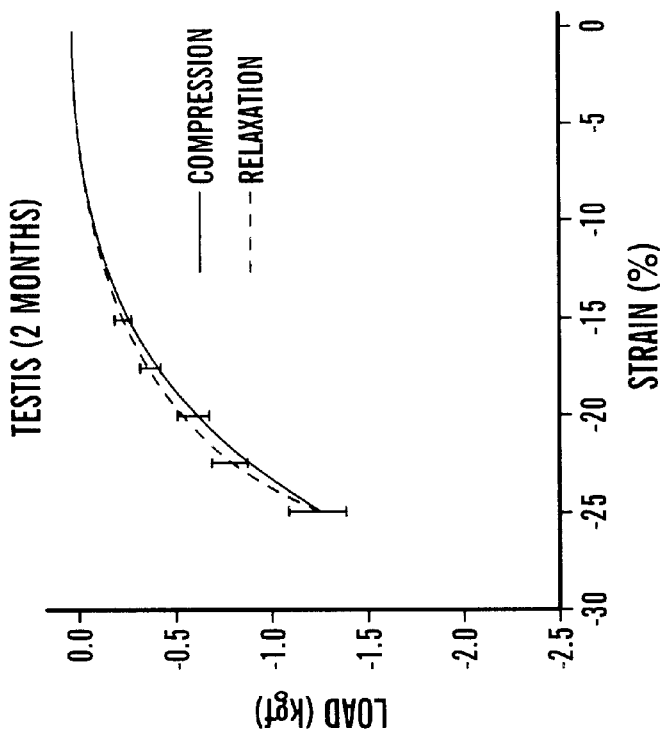
FIGS. 5A–D depicts biomechanical studies of the retrieved testicular prosthesis at 1 month (FIG. 5A); at 2 months (FIG. 5B); at 3 months (FIG. 5C); and polymers only at 1 month (FIG. 5D).
Figure 5A:
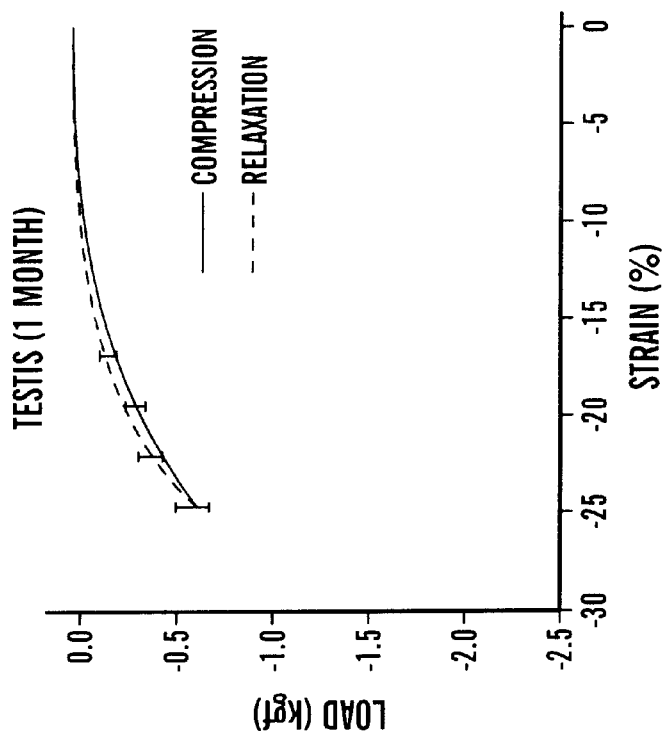
Figure 5D:
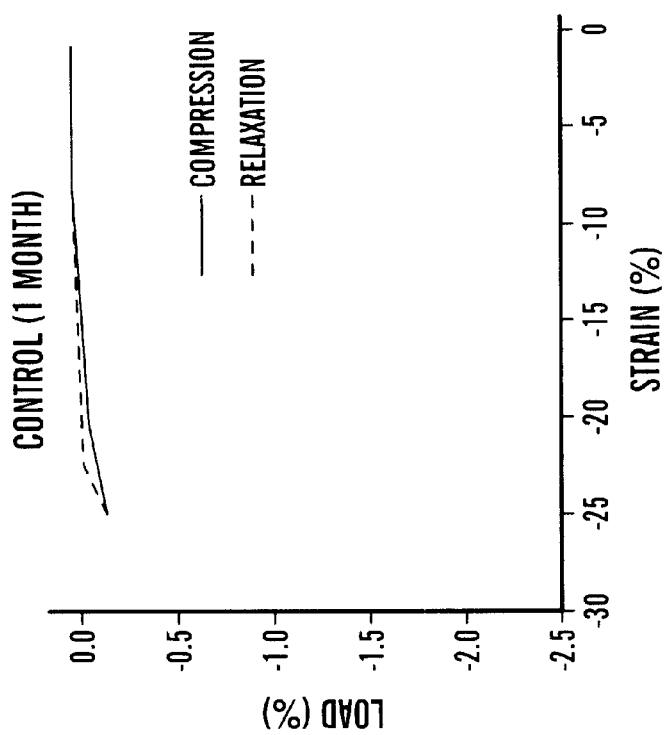
Figure 5C:
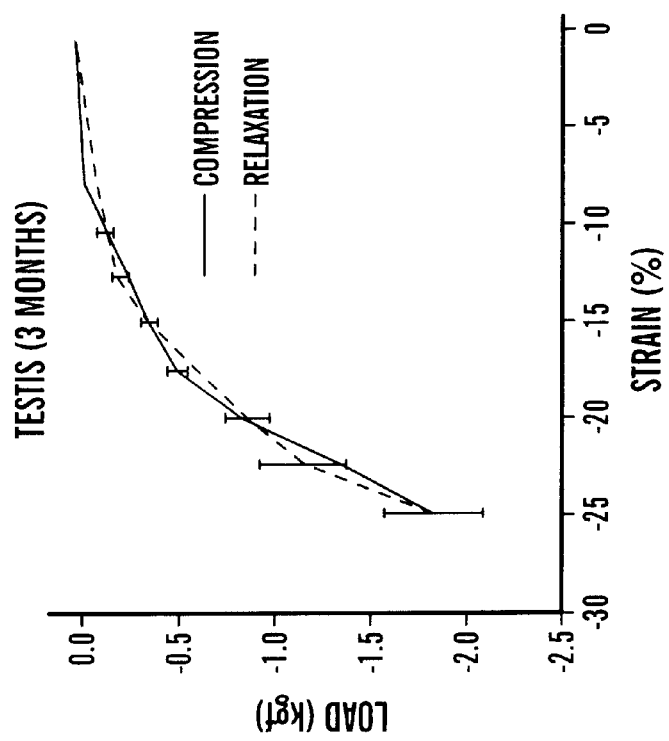
Figure 6:
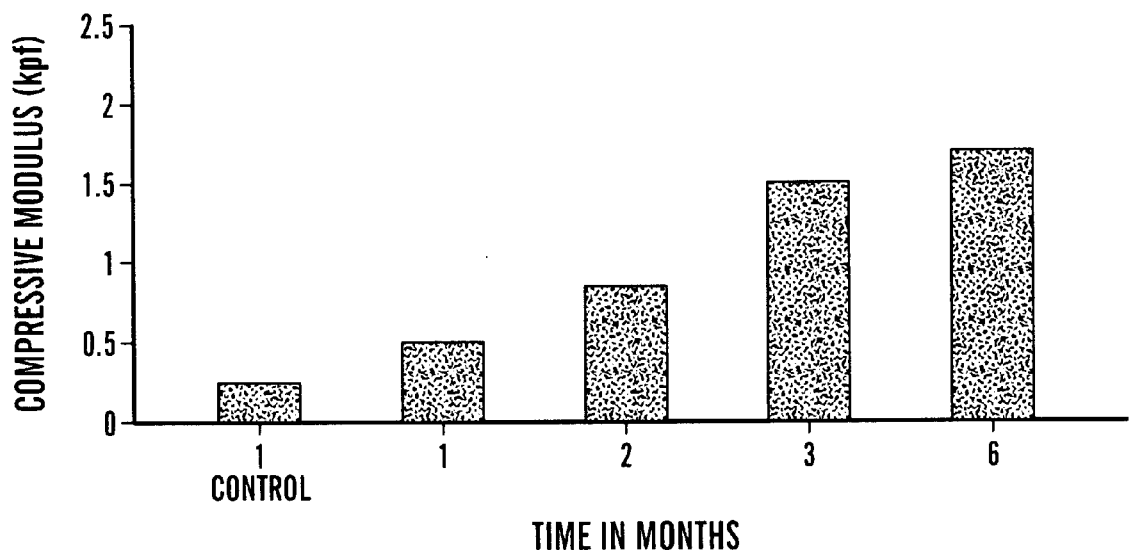
FIG. 6 is a compressive biochemical analyses of the retrieved prostheses demonstrating that the engineered cartilaginous tissue can withstand high degrees of pressures.

In one aspect, as illustrated in FIGS. 1–4, the present invention provides a TE testicular prosthesis (10) for implanting within a patient made from a tissue-engineered scaffold (FIG. 1), comprising a biodegradable polymer scaffold having a substantially elliptical body (20) in longitudinal cross-section to replicate the shape of a testicle (FIG. 2), and a substantially circular cross-section (30) in transverse cross-section (FIG. 3), said biodegradable scaffold defining an interior and an exterior of the prosthesis, and is seeded with disassociated chondrocytes or Leydig cells, or both chondrocytes and Leydig cells. In one embodiment of the invention, as illustrated in FIG. 4, the biodegradable polymer scaffold can have an inner interconnected mesh network (40).

The testicular prostheses engineered with autologous chondrocytes have several advantages over synthetic silicone based prostheses. The seeded scaffold can be cultured in vitro or implanted in vivo in a patient. Preferably, the scaffold is cultured in vitro prior to implantation in a patient. The autologous engineered tissue is biocompatible, non-immunogenic and non-antigenic, thus eliminating some of the problems associated with silicone implantation. The engineered prostheses possess appropriate mechanical characteristics, including their adequate elasticity and resistance to compressive forces. Therefore, prosthesis rupture or breakage would not occur in the in vivo environment.

In another embodiment of the present invention, testosterone, was placed in the central hollow space of the TE testicular prosthesis and was slowly released over the entire study period (40 weeks ex vivo and 16 weeks in vivo). Intramuscular single injection of testosterone enanthate, mimicking the currently used mode of delivery, lasted only up to 4 weeks at therapeutic levels. Testosterone enanthate injection is considered the preferred administration route clinically, due to its relatively longer lasting activity, as compared to oral and transdermal delivery methods. However, this method has its limitations, such as frequent injections and gynecomastia due to the initial high testosterone burst effect.

Preferred polymers include polyglycolic and acid polymers (PGA), polylactic acid polymers (PLA), polysebacic acid polymers (PSA), poly(lactic-co-glycolic) acid copolymers (PLGA), poly(lactic-co-sebacic) acid copolymers (PLSA), poly(glycolic-co-sebacid) acid copolymers (PGSA), and polyhydroxyalkanoate (PHA). PHAs and their production are described in, for example, PCT Publication Nos. WO99/14313, WO99/32536 and WO00/56376. Combinations of biodegradable polymers, e.g., PGA and PLGA, can be used.

Other biodegradable polymers useful in the present invention include polymers or copolymers of caprolactones, carbonates, amides, amino acids, orthoesters, acetals, cyanoacrylates and degradable urethanes, as well as copolymers of these with straight chain or branched, substituted or unsubstituted, alkanyl, haloalkyl, thioalkyl, aminoalkyl, alkenyl, or aromatic hydroxy- or di-carboxylic acids. In addition, the biologically important amino acids Myth reactive side chain groups, such as lysine, arginine, aspartic acid, glutamic acid, serine, threonine, tyrosine and cysteine, or their enantiomers, may be included in copolymers with any of the aforementioned materials. Examples of synthetic biodegradable polymers are described in U.S. Pat. Nos.: 5,431,679; 5,403,347; 5,314,989; and 5,502,159.

Surface properties of any medical device are extremely important, since it is this surface that interacts with the host. Since this invention employs cell seeded scaffolds for tissue engineering, it is not only necessary for the scaffold to be biocompatible and biodegradable, it is also essential that the surface is conducive to cell attachment and subsequent tissue growth. It is therefore desirable to be able to adjust surface properties to suit the intended application, without altering other properties of the scaffold such as its mechanical strength or thermal properties. Useful surface modifications could include, for example, changes in chemical group functionality, surface charge, hydrophobicity, hydrophilicity, and wettability. For example, it would be desirable to improve or maximize cellular attachment or allow for the attachment of the desired cell type or types. This can be accomplished, for example, by attaching or coating the surface with a bioactive compound or peptide which promotes cellular attachment. The coating or bioactive compound may be attached to the surface either covalently or non-covalently. Such skills are well known in the art.

The biodegradable polymer scaffold is configured to replicate the shape of a testicle and is of a substantially elliptical configuration. The prosthetic testicle of the invention can be produced in any size necessary to accommodate the proper testicle size required by a patient.

Sterilization is performed prior to seeding the scaffold. Heat sterilization is often impractical since the heat treatment could deform the device, especially if the materials have a melting temperature below that required for the heat sterilization treatment. This problem can be overcome using cold ethylene oxide gas as a sterilizing agent.

The scaffold is seeded with the chondrocytes prior to implantation. The chondrocytes may be harvested from a healthy section of the individuals tissue, e.g., articular cartilage or epiphysial growth-plate, preferably the ear, expanded in vitro using cell culture techniques and then seeded onto the scaffold. Alternatively, the chondrocytes may be obtained from other donor's tissues or from existing cell lines. Mesenchymal cells obtained from bone marrow can also be differentiated into chondrocytes under appropriate culture conditions as described by, e.g., Butnariu-Ephrat et al., Clinical Orthopaedics and Related Research, 330:234–243, 1996. Other sources from which chondrocytes can be derived include dermal cells and pluripotent stem cells.

The chondrocytes and Leydig cells may be seeded onto the scaffold of the invention by any standard method. In one embodiment of the invention, the scaffold is seeded only with chondrocytes. In another embodiment of the invention, the scaffold is seeded only with Leydig cells. In yet another embodiment of the invention, the scaffold is seeded with a combination of chondrocytes and Leydig cells.

Suitable growth conditions and media for cells in culture are well known in the art. Cell culture media typically comprise essential nutrients, but also optionally include additional elements (e.g., growth factors, salts and minerals) which may be customized for the growth and differentiation of particular cell types. In the preferred embodiments, cell-polymer constructs were suspended in HAMM's F12 medium (Gibco, New York, N.Y.) containing 10% fetal bovine serum with L-glutamine (292 $\mu$g/ml), penicillin (100 $\mu$g/ml) and ascorbic acid (50 $\mu$g/ml). Other media may also be used. For example, "standard cell growth media" include Dulbecco's Modified Eagles Medium, low glucose (DMEN), with 110 mg/L pyruvate and glutamine, supplemented with 10–20% Fetal Bovine Serum (FBS) or 10–20% calf serum (CS) and 100 U/ml penicillin. Other standard media include Basal Medium Eagle, Minimal Essential Media, McCoy's 5A Medium, and the like, preferably supplemented as above (commercially available from, e.g., JRH Biosciences, Lenexa, Kan.; GIBCO, BRL, Grand Island, N.Y.; Sigma Chemical Co., St. Louis, Mo.).

The cell seeded construct may be placed in a bioreactor to form a tissue-engineered testicle or implanted directly in a patient in need thereof. The TE testicular prosthesis is surgically implanted using standard surgical techniques.

It is an additional object of the present invention to provide a TE testicular prosthesis that is therapeutically functional in that it would be able to satisfy the function of a normal testicle by producing testosterone. The prosthesis of the present invention is suited for use in male patients of all ages for whom testicular replacement is indicated either with or without the therapeutic release of testosterone, e.g., children with undescended testicles or torsion of the testicle, and adults with testicular cancer, traumatic injury or orchiectomy. The prosthesis of the present invention is especially suited for use in infants or young children.

The TE testicular prosthesis of the present invention provides for delivery of an androgenic substance, such as testosterone, by incorporating microencapsulated Leydig cells within the interior of the prosthesis. Microencapsulated Leydig cells enable controlled testosterone replacement therapy in addition to offering several advantages, such as serving as a semipermeable barrier between the transplanted cells and the host's immune system, as well as allowing for the long term physiological release of testosterone. Furthermore, microencapsulated Leydig cells are viable and are able to produce testosterone in vitro and in vivo. The microencapsulation system renders the cells non-immunogenic. Thus, the TE testicular prosthesis of the present invention can be used to replace or supplement testosterone in patients with testicular dysfunction.

Cell encapsulation methods hare been used to isolate cells while allowing the release of desired biological materials. It can be applied to all cell types secreting a bioactive substance either naturally or through genetic engineering means. In practice, the main work has been performed with insulin secreting tissue.

Encapsulation procedures are most commonly distinguished by their geometrical appearance, i.e. micro- or macro-capsules. Typically, in microencapsulation, the cells are sequestered in a small permselective spherical container, whereas in macroencapsulation the cells are entrapped in a larger non-spherical membrane, Lim et al. (U.S. Pat. Nos. 4,409,331 and 4,352,883) discloses the use of microencapsulation methods to produce biological materials generated by cells in vitro, wherein the capsules have varying permeabilities depending upon the biological materials of interest being produced, Wu et al, *Int. J. Pancreatology*, 3:91–100 (1988), disclose the transplantation of insulin-producing, microencapsulated pancreatic islets into diabetic rats.

Jordan et al. in U.S. Pat. No. 6,080,412 describes a method of producing a microencapsulated pharmaceutical formulation wherein a dye is attached to the surface of pharmaceutical particles to which a source of radiant energy is applied in the presence of a liquid polymeric material so as to cause the material to cross-link, producing a conformal layer of cross-linked polymer on the particulate surfaces. The polymer is able to provide an immuno-protective layer around the particles, while allowing therapeutic components to exit the microcapsules.

Generally, in microencapsulation, cell clusters are immobilized in 500–600 $\mu$m hydrogel microspheres. Typically the semipermeable membrane is formed at the microsphere surface. Various chemical systems have been used. In the most common form, the capsule membrane is formed by ionic or hydrogen bonds between two weak polyelectrolytes; typically an acidic polysaccharide, such as alginic acid, and a cationic polyaminoacid, such as polylysine. Practically, the entrapment of cells is obtained by the gelation of a charged polyelectrolyte induced by exposure to a multivalent counter-ion. A counter-polyelectrolyte is then interfacially adsorbed on the cell immobilization matrix. Microcapsules possess an ideal shape for diffusion. In vitro tests demonstrated that testosterone release from microencapsulated cells was equivalent to that from normal, unencapsulated cells. They are, however, mechanically fragile, particularly when polyelectrolytes are used.

In another embodiment of the present invention Leydig cells are immortalized with telomerase or by other means before incorporation into the TE testicular prosthesis. Telomerase-immortalized human cells provide more stable, uniform cell populations for long-term gene expression. These cell lines can undergo repeated rounds of genetic engineering making them useful in gene therapy applications. Telomerase is responsible for maintaining telomere length and allows the cells to divide indefinitely while retaining normal function and phenotype. Telomerase-immortalization can be readily performed by methods known in the art. See, e.g., U.S. Pat. No. 5,645,986, entitled "Therapy and Diagnosis of Conditions Related to Telomere Length and/or Telomerase Activity," West et al., issued Jul. 8, 1997, and hereby incorporated by reference herein in its entirety including all figures, drawings, and tables. Other methods exist in the art for generating immortalized cell lines from primary cells, e.g. culturing the cells with cytokines can be used in converting non-immortalized cells into immortalized cells as disclosed in U.S. Pat. No. 6,011,197, Strelchenko et al., issued Jan. 4, 2000 and hereby incorporated by reference herein in its entirety including all figures, drawings, and tables.

It is to be understood that while the invention has been described in conjunction with the preferred specific embodiments thereof that the foregoing description as well as the examples that follow are intended to illustrate and not limit the scope of the invention. Other aspects, advantages and modifications within the scope of the invention will be apparent to those skilled in the art to which the invention pertains.

EXAMPLES

Polymers

Unwoven sheets of polyglycolic acid polymers (density 58 mg/ml) were designed and configured into testis shaped scaffolds with central hollow spaces (0.4 cm in diameter and 1 cm in length). The polymers were composed of fibers of 15 $\mu$m in diameter and an interfiber distance between 0–200 $\mu$m with 95% porosity. The polymer scaffold was designed to degrade via hydrolysis in 6–8 weeks. The resulting flexible scaffold was coated with a liquefied copolymer (poly-L-lactide-co-glycolide 50:50; Sigma; St. Louis, Mo.) 80 mg/ml methylene chloride) in order to achieve adequate mechanical characteristics. The polymers were sterilized in ethylene oxide and stored under sterile conditions.

Cell Isolation, Culture and Seeding

Hyaline cartilage was obtained from the articular surfaces of calf shoulder. The shoulders were washed in povidone-iodine 10% solution, and dissected into 2 to 3 mm tissue fragments. Chondrocytes were isolated under sterile conditions using a previously described technique. See Klagsbrun, M.: Large-scale preparation of chondrocytes, Meth. Enzym. 58:549, 1979.[1,2] Briefly the cartilage tissue fragments were digested in Ham F-12 culture medium containing 3% type II collagenase for 6 to 12 hours (Worthington Biochemical Corp., Lakewood, N.J.). Recovered cells were rinsed in phosphate buffered saline and resuspended in culture medium (Ham's F-12 containing 10% FBS, penicillin 100 U/cm$^3$, streptomycin 100 $\mu$/cm$^3$, ascorbic acid 50 ug/ml: Gibco; Grand Island, N.Y.). Cell number and viability were determined by trypan blue using a hemocytometer under light microscopy. Chondrocytes were plated and grown in culture at 37° C. in 5% $CO_2$ until sufficient number of cells were obtained. Cells were trypsinized, collected, washed and counted for seeding.

Testicular Prosthesis: In Vivo Tissue Formation

Chondrocytes were seeded onto pre-formed poly-L-lactic acid coated polyglycolic acid polymers at a concentration of 50×10$^6$ chondrocytes/cm$^3$. A total of 48 poly-L-lactic acid coated polyglycolic acid polymer scaffolds (32 seeded with cells and 16 without cells) were implanted into the scrotal space of 24 athymic mice. The animals were sacrificed at 1, 2, 3 and 6 months after implantation for analyses (n=12 samples per time point).

Testicular Prosthesis: In Vitro Functional Studies

Chondrocytes were seeded onto 10 pre-configured testis shaped polymers at a concentration of 100×10$^6$ chondrocytes/cm$^3$. Five days after seeding, the cell-polymer constructs, which were placed in static conditions (37°, 5% $CO_2$), were suspended freely and maintained in a bioreactor for 4 weeks to form cartilage tissue. Subsequently, testosterone enanthate (100 $\mu$g) was injected into the central hollow space of each testicular prosthesis, and maintained for 40 weeks in culture. A sample of medium was collected every 2 days for testosterone level detection assays.

Testicular Prosthesis: In Vivo Functional Studies

A separate group of ex-vivo engineered testicular prostheses was implanted into the scrotal space of castrated athymic mice (n=10). Intratesticular injection of testosterone enanthate was made in each prosthesis at a concentration of 100 $\mu$g. Control groups consisted of animals with castration only (n=8) and sham operations (n=5). Blood samples from every animal were collected, prior and 2 weeks after castration, 1 day after testosterone administration, and weekly up to 16 weeks for circulating testosterone level measurement. The engineered testicular prostheses were retrieved at sacrifice for histomorphological and immunocytochemical analyses.

Histological and Microscopic Analyses

Five micron sections of formalin fixed paraffin embedded tissues were cut and stained with hematoxylin and eosin (H&E), aldehyde fuschin-alcian blue, safranin-O, toluidine blue and Masson's trichrome. Scanning electron microscopy was performed in order to determine the distribution and extent of cartilage tissue formation within the polymer scaffolds prior and at 1, 2, 3 and 6 months after implantation. The specimens were fixed in 1% (v/v) buffered glutaraldehyde and 0.1% (v/v) buffered formaldehyde for 30 minutes and 24 hours, respectively. After dehydration with a graded ethanol series, the samples were air-dried. The dried samples were mounted on aluminum supports and sputter coated with gold. The samples were visualized using a scanning electron microscope (JOEL, model JSM-35, Peabody, Mass.) with a voltage of 25-kV.

Biomechanical Studies

Mechanical properties of the tissue-engineered testicular prosthesis were assessed using a mechanical tester (model 5542, Instron corp, Canton, Mass.) with a 500 N-maximum load cell (n=3). The longitudinal axis of each specimen was compressed until it reached 80% of the initial thickness and released to its initial position at a cross-head speed of 0.5 in/min. The compressive modulus was obtained from the slope of the initial linear section of the stress-strain curve.

Collagen Content Assay

The total collagen content per unit dry weight of the engineered prosthesis samples was determined from the hydroxyproline concentration, and reaction with p-dimethylaminobenzaldehyde and chloramine-T (n=3 per time point). Briefly, the retrieved tissue samples were lyophilized, homogenized and hydrolyzed (6N HCl at 130° C. for 3 hrs) in order to obtain tissue extracts. After neutralization with 2.5 N NaOH, hydroxyproline oxidation was initiated by adding 1 ml. chloramine-T to the extract. After gentle mixing and incubation for 20 minutes, the chloramine-T was inactivated by the addition of 1 ml. perchloric acid to each tube. Finally, 1 ml. p-dimethylaminobenzaldehyde solution was added and incubated for color development. The absorbency of the solution was measured using a spectrophotometer at 550 nm. The standard curve was plotted using a linear regression analysis.

Hormone Detection Assay

Testosterone levels, contained in the collected samples, were determined by radioimmunoassay.[3] Briefly, One ml of $I^{125}$ testosterone (DPC; Los Angeles, Calif.) was added to tubes containing 50 $\mu$l testing samples. The tubes were incubated for 3 hours at 37° C. and decanted thoroughly, removing all visible moisture. After removing the residual droplets, the tubes were placed in an automatic gamma counter (Lbk Wallac, Monterey, Calif.). Calculation of results was obtained by plotting percent bound on the vertical (probability) axis against concentration on the horizontal (logarithmic) axis for each of the non-zero calibrators.

In Vivo Cartilage Formation

All animals tolerated the implants or the duration of the study without any noticeable complications. Gross examination at retrieval showed the presence of well formed milky white cartilage structures within the scrotum. There was no evidence of erosion or infection in any of the implantation sites. The average wet and dry weights of the retrieved specimens increased gradually until 3 months, and remained constant at 6 months after implantation.

Compressive biomechanical analyses of the retrieved prostheses demonstrated that the engineered cartilaginous tissues were readily elastic and withstood high degrees of pressures. The compression modulus, obtained from the slope of the initial linear section of the stress-strain curve was 0.22, 0.49, 0.8, 1.47 and 1.67 kgf at 1, 2, 3 and 6 months, respectively (FIGS. 5A–D).

Scanning electron microscopy of the pre-implanted cell polymer scaffolds demonstrated uniform cell attachment on the polymer fibers. The cartilage prostheses retrieved at 1 month after implantation demonstrated formation of extracellular matrices, occupying interfibrillar spaces within the polymer scaffolds. Undegraded polymer fibers were evident at 1 month. Solid cartilage tissue structures were present by 3 months after implantation.

Histologically, all of the experimental specimens seeded with cells demonstrated mature chondrocytes accompanied by a basophilic extracellular tissue matrix at all time points. Presence of undegraded polymer fibers were evident at 1 month after implantation and continued to degrade over time. The control scaffolds without cells failed to show cartilage tissue formation at all time points. Aldehyde fuschin-alcian blue, toluidine blue, Safranin-O and Masson's trichrome staining further confirmed the presence of cartilage tissue.

Figure 7:
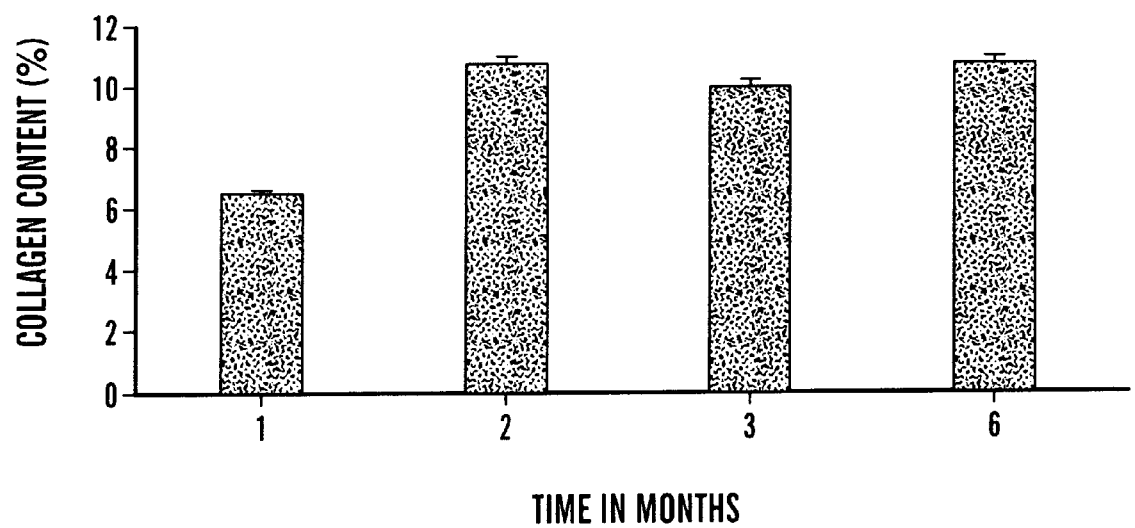
FIG. 7 is a collagen content assay which shows that the testicular prostheses seeded with cells had an average collagen composition fraction of 6.5% and 10.8% of the total dry weight at 1 and 2 months, respectively, and remained constant up to 6 months after implantation.

Collagen content assays demonstrated that the testicular prostheses seeded with cells had an average collagen composition fraction of 6.5% and 10.8% of the total dry weight at 1 and 2 months, respectively, and remained constant up to 6 months after implantation (FIG. 7). The collagen fraction measurements of the control implants without cells were negative.

Testicular Prosthesis: In Vitro Functional Studies

Figure 8A:
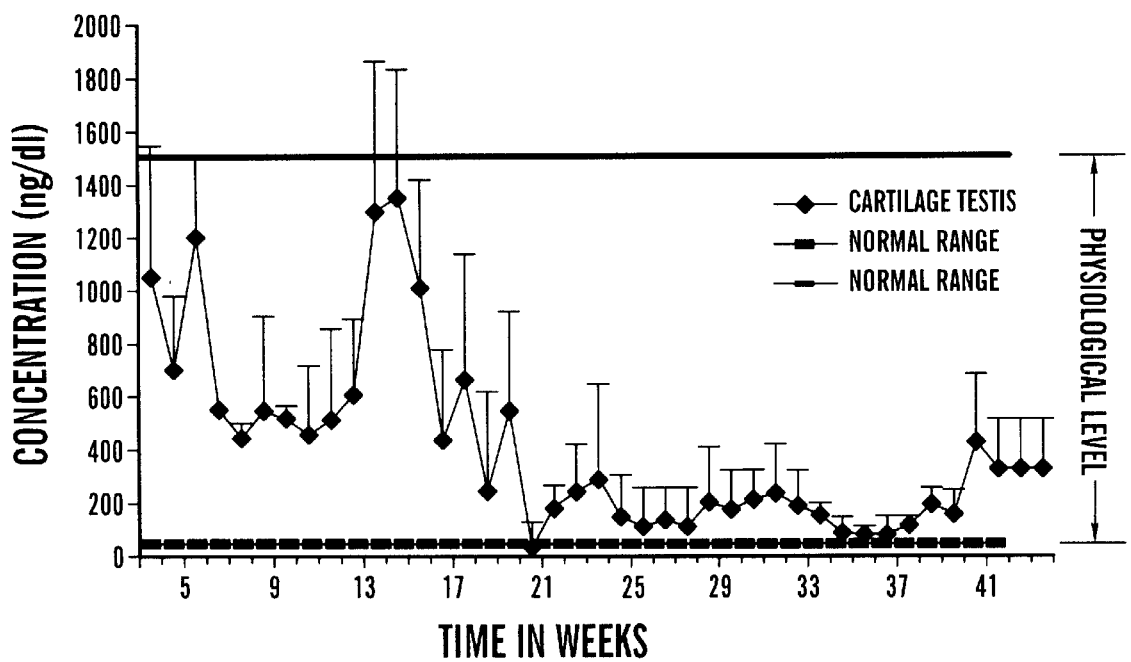
FIGS. 8A–B depict an ex-vivo prostheses injected with testosterone enanthane 100 µg, and shows physiologic testosterone levels throughout the entire study period.
Figure 8B:
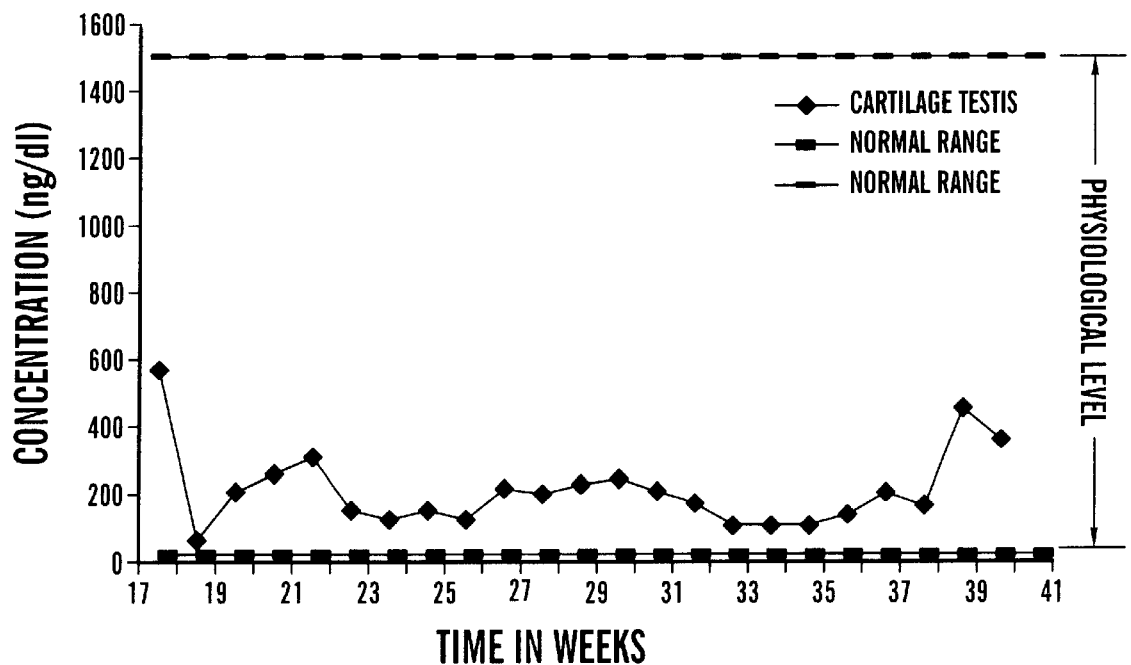

Milky white cartilage testicular prostheses were formed by 4 weeks in every instance. The ex-vivo prostheses, injected with testosterone enanthate 100 $\mu$g. showed an initial burst effect of testosterone followed by a broad plateau for 16 weeks (>500 ng/dl) and gradually decreased until 40 weeks. The detected testosterone levels were physiologic throughout the entire study period (40 weeks) (FIGS. 8A–B). The accumulated amount of the released testosterone was calculated as 60% of the initial injection concentration. Histological analyses of all constructs formed in the bioreactor demonstrated cartilaginous tissue structures, composed of mature chondrocytes surrounded by extracellular matrices.

Testicular Prosthesis: In Vivo Functional Studies

Figure 9A:
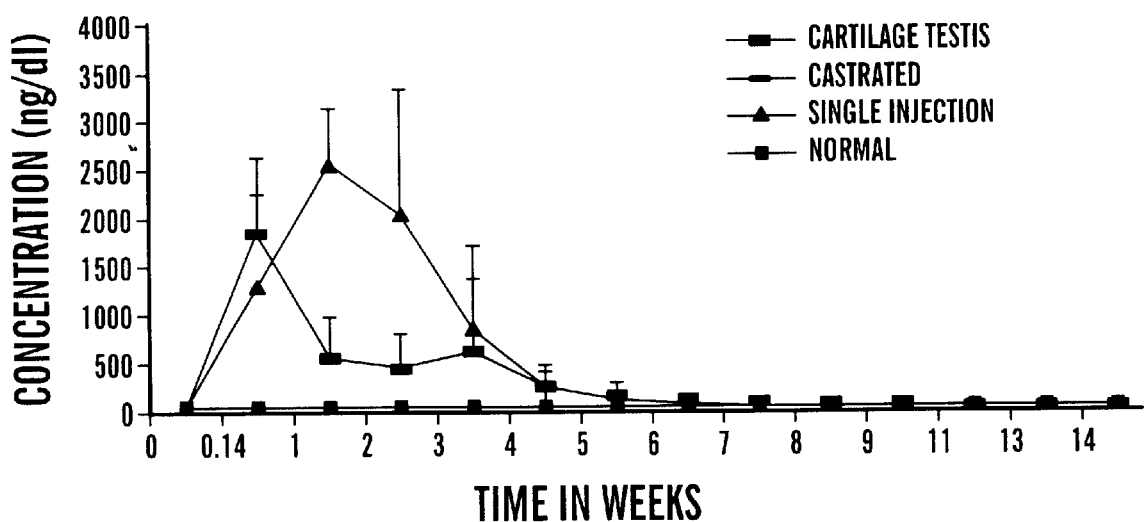
FIGS. 9A–B show that the circulating testosterone levels in the animals implanted with testosterone containing prostheses maintained continued physiologic levels during the entire study period.
Figure 9B:
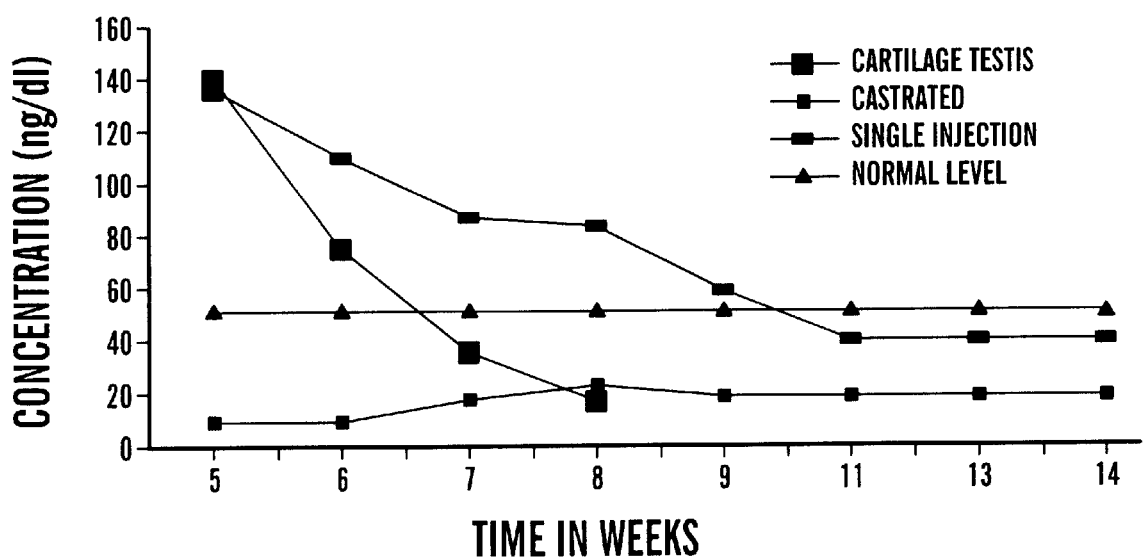

All animals tolerated the implants during the entire period of the study. There was no evidence of erosion or infection in any of the implanted animals. The circulating testosterone levels in the animals implanted with testosterone containing prostheses demonstrated a maximum peak on day one and maintained a continued physiologic range during the entire study period (16 weeks). The control animals that received a single dose intramuscular injection demonstrated a burst level of testosterone during the first 3 weeks and decreased to a castrate levels by 7 weeks after administration (FIG. 9). Histologically, the retrieved testicular implants showed mature chondrocytes with a hollow spacious center in each of the prosthesis.

The references cited herein, as set forth above and below, are incorporated herein by reference in their entirety.

References

1. Yoo J J, Park H J, Lee I, Atala A: Autologous engineered cartilage rods for penile reconstruction. J Urol 162:1119–1121, 1999.
2. Yoo J J, Lee I, Atala A: Cartilage rods as a potential material for penile reconstruction. J Urol 160, 1164–1168, 1998.
3. Pekary E. and Heshman J. M.: Hormone assays. In: Endocrinology and Metabolism. 3rd ed. Edited by Feling P., Baxter. J. D., Lawrence A., Frohman. L., A. Mcgraw-Hill, chapt 6, pp. 201.
4. Elder, J. S., M. A. Keating, and J. W. Duckett, Infant testicular prostheses. J Urol, 1989, 141(6): p. 1413–5.
5. Bain, J., Sexual development, maturation, and behavior. Compr Ther, 1983, 9(6): p. 21–31.
6. Findlay, S., Podolsky. D.: Danger: implants. U.S. News World Rep 1992, 113: 62–67, 1992.
7. Atala A: Autologous cell transplantation for urologic reconstruction. J Urol 159: 2–3, 1998.
8. Yoo J J, and Atala A: A novel gene delivery system using urothelial tissue engineered neo-organs. J Urol 158:1066–1070, 1997.
9. Yoo J J, Meng J, Oberpenning F, and Atala A: Bladder augmentation using allogenic bladder submucosa seeded with cells. Urol 51: 221–225, 1998.
10. Yoo J J, Satar N, Retik A B, Atala A: Ureteral replacement using biodegradable polymer scaffolds seeded with urothelial and smooth muscle cells. J Urol 153:4 (supp), 1995.
11. Cilento B G, Retik A B, Atala A: Urethral reconstruction using a polymer scaffolds seeded with urothelial and smooth muscle cells. J Urol 155:5 (supp), 1996.
12. Amiel G E and Atala A: Current and future modalities for functional renal replacement. Urol Clin 26:235–246, 1999.
13. Park H J, Yoo J J, Kershen R T, Atala A: Reconstruction of human corporal smooth muscle and endothelial cells in vivo. J Urol 162, 1106–1109, 1999.
14. Yoo J J, Park H J, Atala A: Tissue engineering applications for phallic reconstruction. W J Urol 18, 62–66, 2000.
15. Amiel G E, Yoo J J, Kim B S, Atala A: Ex vivo engineered stents for urethral strictures. J Urol, 2001.(in press)
16. Atala A, Cima L G, Kim W, Paige K T, Vacanti J P, Retik A B, Vacanti C A: Injectable alginate seeded with chondrocytes as a potential treatment for vesicoureteral reflux. J Urol 150:745–747, 1993.
17. Atala A, Kim W, Paige K T, Vacanti C A, Retik A B: Endoscopic treatment of vesicoureteral reflux with chondrocyte-alginate suspension. J Urol 152:641–643, 1994.
18. Diamond D A, Caldamone A A. Endoscopic correction of vesicoureteral reflux in children using autologous chondrocytes: preliminary results. J Urol 162(3 Pt 2):1185–8, 1999.

What is claimed is:

1. A tissue-engineered testicular prosthesis, comprising:
a biodegradable polymer scaffold having a substantially elliptical body and a substantially circular cross section, said scaffold defining an interior and an exterior of the prosthesis, and wherein said scaffold is seeded with disassociated chondrocytes.

2. The testicular prosthesis of claim 1, wherein the scaffold further comprises Leydig cells.

3. The testicular prosthesis of claim 1, wherein the chondrocytes are autologous.

4. The tissue-engineered testicular prosthesis of claim 1, wherein the interior of said prosthesis is at least partially filled with testosterone.

5. The tissue-engineered testicular prosthesis of claim 1, further comprising microcapsuled living cells capable of producing and secreting a pharmaceutically active substance within the interior of the prosthesis.

6. The tissue-engineered testicular prosthesis of claim 5, wherein the living cells comprise Leydig cells or clusters of Leydig cells.

7. The tissue-engineered testicular prosthesis of claim 5, wherein the pharmaceutically active substance is testosterone.

8. The tissue-engineered testicular prosthesis of claim 5, wherein the living cells are immortalized.

9. A testicular prosthesis, comprising:
a biodegradable polymer scaffold having a substantially elliptical body and a substantially circular cross section, said scaffold defining an interior and an exterior of the prosthesis, and wherein said scaffold is seeded with Leydig cells.

10. A testicular prosthesis, comprising:
a biodegradable polymer scaffold, said scaffold defining an interior and an exterior of the prosthesis, and wherein said scaffold is seeded with both chondrocytes and Leydig cells.

11. The testicular prosthesis of claims 1, 9 or 10 wherein the biodegradable polymer comprises a polyglycolic acid.

12. The testicular prosthesis of claim 11, wherein the biodegradable polymer further comprises a poly-L-lactide-co-glycolide.

13. A method of treating testicular dysfunction, comprising:
implanting a device of claim 1, 9 or 10 into a patient in need thereof.

14. A method of producing tissue-engineered testicular prosthesis, comprising:
providing a biodegradable polymer scaffold having a substantially elliptical body and a substantially circular cross section; and seeding said scaffold with disassociated chondrocytes.

15. The method of claim 14, further comprising subjecting said prosthesis to a bioreactor in vitro.

16. The method of claim 14, further comprising seeding said scaffold with Leydig cells.

* * * * *